United States Patent [19]

Stoltefuss et al.

[11] Patent Number: 5,204,472

[45] Date of Patent: Apr. 20, 1993

[54] QUINOLINE AND ISOQUINOLINE INTERMEDIATES

[75] Inventors: Jürgen Stoltefuss; Horst Böshagen, both of Haan; Siegfried Goldmann, Wuppertal; Alexander Straub, Wuppertal; Rainer Gross, Wuppertal; Joachim Hütter, Leverkusen; Siegbert Hebisch; Martin Bechem, both of Wuppertal, all of Fed. Rep. of Germany

[73] Assignee: Bayer Aktiengesellschaft, Leverkusen, Fed. Rep. of Germany

[21] Appl. No.: 807,523

[22] Filed: Dec. 13, 1991

Related U.S. Application Data

[62] Division of Ser. No. 677,718, Mar. 29, 1991, Pat. No. 5,100,900.

[30] Foreign Application Priority Data

Apr. 6, 1990 [DE] Fed. Rep. of Germany ....... 4011105

[51] Int. Cl.$^5$ ................ C07D 401/04; C07D 219/02; C07D 215/12
[52] U.S. Cl. .................................... 546/168; 546/144; 546/167
[58] Field of Search ........................ 546/168, 167, 144

[56] References Cited

U.S. PATENT DOCUMENTS

| | | | |
|---|---|---|---|
| 2,359,329 | 10/1944 | Phillips et al. | 546/167 |
| 2,400,500 | 5/1946 | Gibbs | 546/167 |
| 3,943,140 | 3/1976 | Bossert et al. | 546/167 |
| 4,049,662 | 9/1977 | Meyer et al. | 546/167 |
| 4,483,985 | 11/1984 | Wehinger et al. | 546/167 |

FOREIGN PATENT DOCUMENTS

| | | |
|---|---|---|
| 125741 | 7/1944 | Australia .............. 546/167 |
| 0002208 | 11/1978 | European Pat. Off. . |
| 123095 | 3/1984 | European Pat. Off. . |
| 123112 | 3/1984 | European Pat. Off. . |
| 2210667 | 3/1972 | Fed. Rep. of Germany . |
| 2117571 | 11/1972 | Fed. Rep. of Germany . |
| 2658804 | 7/1978 | Fed. Rep. of Germany . |
| 582254 | 11/1946 | United Kingdom ............ 546/167 |

OTHER PUBLICATIONS

Journal of Medicinal Chemistry, vol. 13, No. 5, Sep. 1970, pp. 860–864; J. S. Gillespie Jr. et al.
Journal of Heterocyclic Chemistry, vol. 6, No. 2, Apr. 1969, pp. 243–245; J. B. Wommack et al.

*Primary Examiner*—David B. Springer
*Attorney, Agent, or Firm*—Sprung Horn Kramer & Woods

[57] ABSTRACT

Positive inotropically active 4-quinolyl-dihydropyridines of the formula

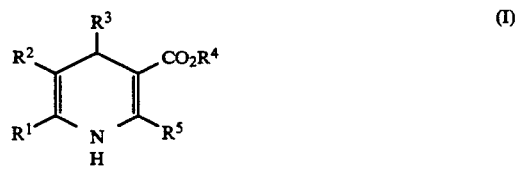

(I)

in which
$R^1$ and $R^5$ are identical or different and represent straight-chain or branched alkyl having up to 8 carbon atoms,
$R^2$ represents nitro or cyano, or
$R^1$ and $R^2$ together form a lactone ring of the formula

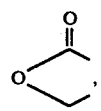

$R^3$ represents a radical of the formula

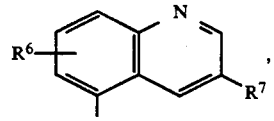

(Abstract continued on next page.)

-continued
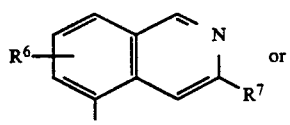
or
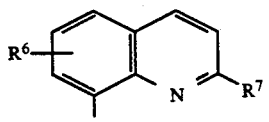
in which
R⁶ —denotes hydrogen, halogen or straight-chain or branched alkyl or alkoxy in each case having up to 8 carbon atoms,
R⁷ denotes aryl, thienyl or pyridyl, and
R⁴ represents hydrogen, or optionally substituted alkyl, alkenyl, alkadienyl or alkynyl,
and their physiologically acceptable salts.
4 Claims, No Drawings

QUINOLINE AND ISOQUINOLINE INTERMEDIATES

This is a division, of application Ser. No. 677,718, filed Mar. 29, 1991, now U.S. Pat. No. 5,100,960.

The invention relates to new 4-quinolyl- and 4-isoquinolyl-dihydropyridines, processes for their preparation and their use in medicaments, in particular in agents having positive inotropic action.

It is already known that 1,4-dihydropyridines have vasodilator properties and can be used as coronary agents and antihypertensives [compare Brit. Patent 1,173,062 and 1,358,951; DE-OS (German Offenlegungsschrift) 2,629,892 and 2,752,820]. It is furthermore known that 1,4-dihydropyridines cause an inhibition of the contractility of smooth and cardiac muscles and can be employed for the treatment of coronary and vascular disorders [compare Fleckenstein, Ann. Rev. Pharmacol. Toxicol., 17, 149–166 (1977)].

It is additionally known that, in addition to a positive inotropic cardiac action, 3-nitro-dihydropyridines in general can show the disadvantage of an undesired constricting action on the coronary vasculature [compare Schramm et al., Nature 303, 535–537 (1983) and DE-OS (German Offenlegungsschrift) 3,447,169].

With knowledge of the prior art, it was unforeseeable that the compounds according to the invention would have a positive inotropic action on the cardiac muscle, increasing the contractility and having essentially neutral vascular behavior.

The invention relates to new substituted dihydropyridines of the general formula (I)

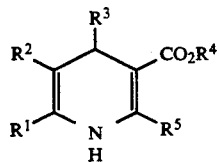

in which
$R^1$ and $R^5$ are identical or different and represent straight-chain or branched alkyl having up to 8 carbon atoms,
$R^2$ represents nitro or cyano, or
$R^1$ and $R^2$ together form a lactone ring of the formula

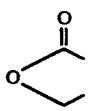

$R^3$ represents a radical of the formula

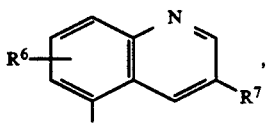

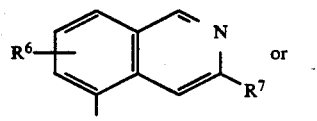 or

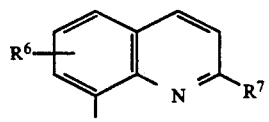

in which
$R^6$ -denotes hydrogen, halogen or straight-chain or branched alkyl or alkoxy in each case having up to 8 carbon atoms,
$R^7$-denotes aryl having 6 to 10 carbon atoms, which is optionally monosubstituted or disubstituted by identical or different substituents from the series comprising halogen, nitro, cyano, trifluoromethyl, trifluoromethoxy, trifluoromethylthio, straight-chain or branched alkyl, alkoxy or alkoxycarbonyl in each case having up to 8 carbon atoms and carboxyl, or denotes thienyl or pyridyl, which are optionally monosubstituted by halogen,
$R^4$ represents hydrogen, or represents a straight-chain or branched alkyl, alkenyl, alkadienyl or alkynyl in each case having up to 10 carbon atoms, which are optionally monosubstitued or disubstituted by identical or different substituents from the series comprising halogen, hydroxyl, carboxyl, cyano, nitro, phenoxy or straight-chain or branched alkyl thio, alkoxy, alkoxy carbonyl, acyl or acyloxy in each case having up to 8 carbon atoms and phenoxy or phenyl, where the latter can in turn be monosubstituted or disubstitued by identical or different substituents from the series comprising halogen and straight-chain or branched alkyl or alkoxy in each case having up to 6 carbon atoms, and their physiologically acceptable salts.

The physiologically acceptable salts can be salts of the compounds according to the invention with inorganic or organic acids. Preferred salts are those with organic acids such as, for example, hydrochloric acid, hydrobromic acid, phosphoric acid or sulphuric acid, or salts with organic caboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention exist in stereoisomeric forms which behave either as image and mirror image (enantiomers), or which do not behave as image and mirror image (diastereomers). The invention relates both to the antipodes and to the racemic forms and the diastereomer mixtures. Like the diastereomers, the racemic forms can be separated into the stereoisomerically uniform components in a known manner (compare E. L. Eliel, Stereochemistry of Carbon Compounds, McGraw Hill, 1962).

Preferred compounds of the general formula (I) are those in which
$R^1$ and $R^5$ are identical or different and represent straight-chain or branched alkyl having up to 6 carbon atoms,
$R^2$ represents nitro or cyano, or
$R^1$ and $R^2$ together form a lactone ring of the formula

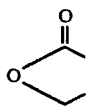

$R^3$ represents a radical of the formula

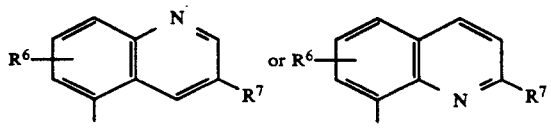

in which $R^6$-denotes hydrogen, fluorine, chlorine or straight-chain or branched alkyl or alkoxy in each case having up to 2 carbon atoms, $R^7$-denotes phenyl which is optionally substituted by fluorine, chlorine, nitro, cyano, trifluoromethyl or by straight-chain or branched alkyl or alkoxy in each case having up to 6 carbon atoms, or denotes thienyl or pyridyl, which are optionally monosubstituted by fluorine or chlorine, $R^4$-represents hydrogen or represents straight-chain or branched alkyl or alkenyl in each case having up to 8 carbon atoms, which are optionally substituted by fluorine, chlorine, hydroxyl, carboxyl, cyano, nitro or by straight-chain or branched alkylthio, alkoxy, alkoxycarbonyl, acyl or acyloxy in each case having up to 6 carbon atoms or by phenoxy or phenyl, and their physiologically acceptable salts.

Particularly preferred compounds of the general formula (I) are those in which $R^1$ and $R^5$ are identical or different and represent a straight-chain or branched alkyl having up to 4 carbon atoms, $R^2$ represents nitro or cyano, or $R^1$ and $R^2$ together form a lactone ring of the formula

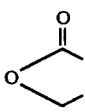

$R^3$ represents a radical of the formula

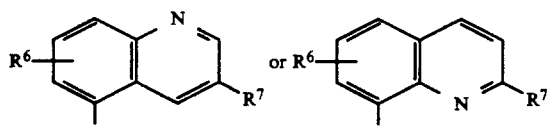

in which $R^6$-denotes hydrogen, chlorine or methyl, $R^7$-denotes phenyl which is optionally substituted by fluorine, chlorine, nitro, trifluoromethyl or by straight-chain or branched alkyl or alkoxy in each case having up to 4 carbon atoms, or denotes thienyl or pyridyl, which are optionally monosubstituted by fluorine or chlorine, $R^4$-represents hydrogen, or represents a straight-chain or branched alkyl having up to 6 carbon atoms, which is optionally substituted by hydroxyl, carboxyl, cyano or by straight-chain or branched alkoxycarbonyl, alkoxy or acyloxy in each case having up to 6 carbon atoms, and their physiologically acceptable salts.

Additionally, a process for the preparation of the compounds of the general formula (I) according to the invention has been found, characterized in that in the case in which $R^1$ and $R^2$ have the abovementioned meanings, but do not together form a lactone ring,

[A] compounds of the general formula (II)

$$R^3\text{—CHO} \qquad (II)$$

in which $R^3$ has the abovementioned meaning, are first reacted with acetoacetates of the general formula (III)

$$R^5\text{—CO—CH}_2\text{—CO}_2\text{—R}^4 \qquad (III)$$

in which $R^4$ and $R^5$ have the abovementioned meanings, if appropriate with the isolation of the corresponding ylidene compounds of the general formula (IV)

$$R^3\text{—CH=C—CO}_2\text{—R}^4 \atop {\text{CO—R}^5} \qquad (IV)$$

in which $R^3$, $R^4$ and $R^5$ have the abovementioned meanings, and are then reacted either with compounds of the formula (V)

$$R^1\text{—CO—CH}_2\text{—R}^2 \qquad (V)$$

in which $R^1$ and $R^2$ have the abovementioned meanings, in the presence of ammonia or ammonium salts, or directly with amino derivatives of the general formula (VI)

$$R^1\text{—C=CH—R}^2 \atop {\text{NH}_2} \qquad (VI)$$

in which $R^1$ and $R^2$ have the abovementioned meanings, if appropriate in the presence of inert organic solvents, or

[B] the aldehydes of the general formula (II) are first reacted with the compounds of the general formula (V), if appropriate with the isolation of the ylidene compounds of the general formula (VII)

$$R^3\text{—CH=C—R}^2 \atop {\text{CO—R}^1} \qquad (VII)$$

in which $R^1$, $R^2$ and $R^3$ have the abovementioned meanings, and in a next step are reacted with the above-mentioned compounds of the general formula (III) in inert solvents, in the presence of ammonia or ammonium salts or directly with enaminocarboxylic acid derivatives of the general formula (VIII)

$$R^5\text{—C=CH—CO}_2\text{—R}^4 \atop {\text{NH}_2} \qquad (VIII)$$

in which $R^4$ and $R^5$ have the abovementioned meanings, or in the case in which $R^1$ and $R^2$ together form a lactone ring,

[C] first, according to the methods mentioned under [A] and [B], compounds of the general formula (Ia)

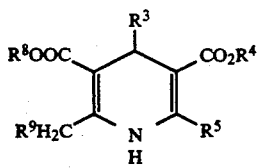

(Ia)

in which $R^3$, $R^4$ and $R^5$ have the abovementioned meanings, $R^8$ represents a $C_1$-$C_6$-alkyl radical and $R^9$ represents a leaving group such as, for example, chlorine or acetoxy, are prepared and an acid-or base-catalyzed ring closure according to known processes is added, and in the case in which $R^4$ does not denote hydrogen,

[D] compounds of the general formula (I), in which $R^1$, $R^2$, $R^3$, $R^4$ and $R^5$ have the abovementioned meanings and $R^4$ represents hydrogen, are reacted, if appropriate via a reactive acid derivative, with the corresponding alcohols, the corresponding enantiomers of the esters being obtained by use of the enantiomerically pure carboxylic acids ($R^4$=H).

The processes according to the invention can be illustrated by the following equations:

[A]

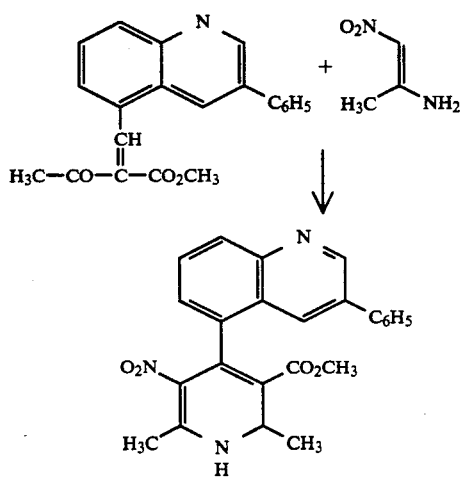

[B]

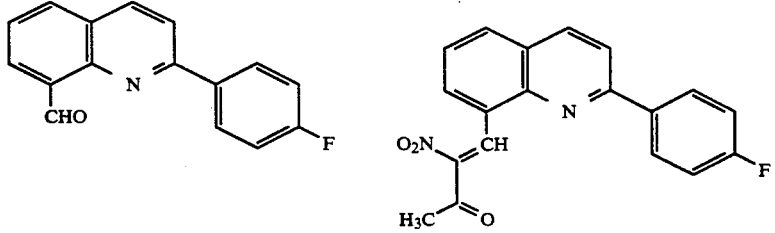

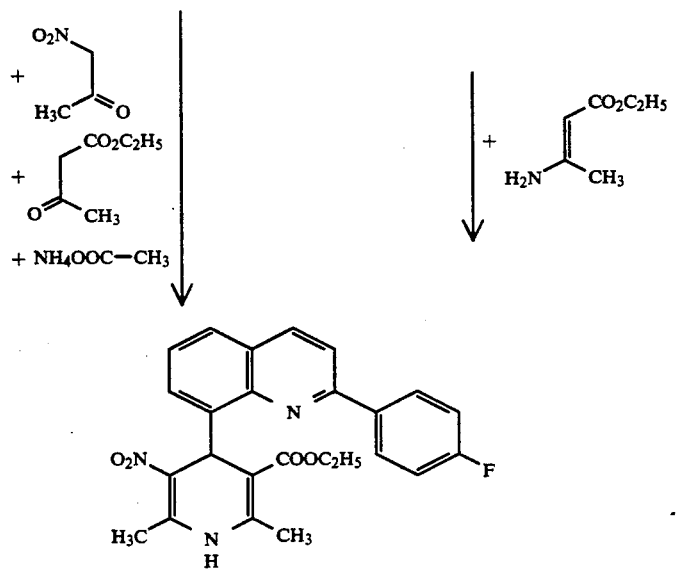

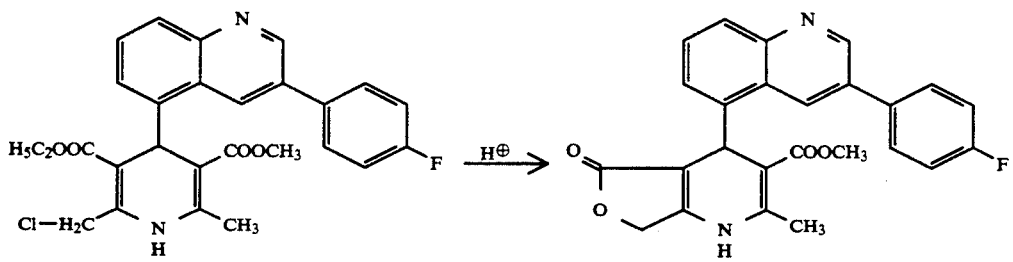

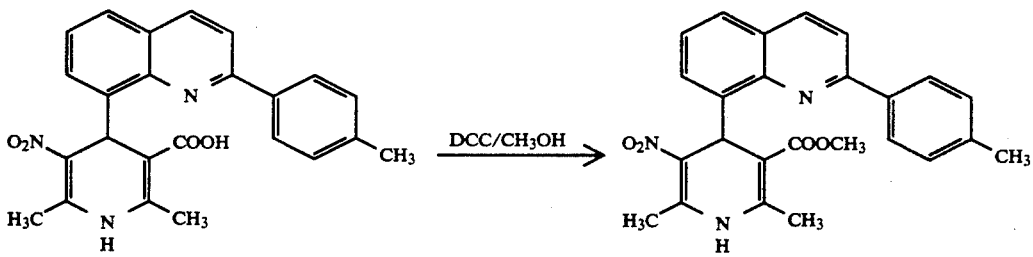

Suitable solvents for processes [A], [B] and [C] are all inert organic solvents. These preferably include alcohols such as methanol, ethanol, n- or iso-propanol, ethers such as diethyl ether, tetrahydrofuran, dioxane or glycol monomethyl ether or glycol dimethyl ether, glacial acetic acid, pyridine, dimethylformamide, dimethyl sulphoxide, acetonitrile or hexamethylphosphoric triamide or toluene.

Suitable solvents for process [D] are the above-mentioned solvents with the exception of the alcohols.

The reaction temperature for processes [A], [B], [C] and [D] can be varied within a relatively wide range. In general, the reaction is carried out in a range from 10° C. to 200° C., preferably from 20° C. to 150° C.

The processes can be carried out at normal pressure, or elevated or reduced pressure (for example from 0.5 to 5 bar), preferably at normal pressure.

When carrying out the process according to the invention, any desired ratio of the substances participating in the reaction can be used. However, in general the reaction is carried out with molar amounts of the reactants.

Suitable reagents for the activation of the carboxylic acid are the customary reagents such as inorganic halides, for example thionyl chloride, phosphorus trichloride or phosphorus pentachloride, or carbonyldiimidazole, carbodiimides such as cyclohexylcarbodiimide or 1-cyclohexyl-3-[2-(N-methylmorpholino)ethyl]-carbodiimide-p-toluenesulphonate or N-hydroxyphthalimide or N-hydroxy-benzotriazole.

Enantiomerically pure forms are obtained, for example, by separating diastereomer mixtures of the compounds of the general formula (I) in which $R^4$ represents an optical ester radical by a customary method, then preparing the enantiomerically pure caboxylic acids and then optionally converting into the enantiomerically pure dihydropyridines by esterification with appropriate alcohols.

Suitable chiral ester radicals are all esters of enantiomerically pure alcohols such as, for example, 2-butanol, 1-phenylethanol, lactic acid, lactic acid esters, mandelic acid, mandelic acid esters, 2-amino alcohols, sugar derivatives and many more other enantiomerically pure alcohols.

The diastereomers are in general separated either by fractional crystallization, by column chromatography or by Craig partition. Which is the optimum process must be decided from case to case, and sometimes it is also expedient to utilize combinations of the individual processes. Separation by crystallization or Craig partition or a combination of both processes is particularly suitable.

The enantiomerically pure dihydropyridines are preferably esterified in ethers such as diethyl ether or tetrahydrofuran, dimethylformamide, methyl chloride, chloroform, acetonitrile or toluene.

The aldehydes of the general formula (II) are also new and can be prepared by a process in which a) either compounds of the general formula (IX)

$$R^3-CH_3 \qquad (IX)$$

in which $R^3$ has the abovementioned meaning, are oxidized directly to compounds of the formula (II), or first halogenated to give compounds of the general formula (X)

$$R^3-CH_2-Hal \qquad (X)$$

in which $R^3$ has the abovementioned meaning and

Hal represents halogen, preferably bromine, then reacted with acetate ions and hydrolyzed to give compounds of the formula (XI)

$$R^3-CH_2-OH \qquad (XI)$$

in which $R^3$ has the abovementioned meaning, and these are then oxidized to compounds of the formula (II), or in which b) compounds of the general formula (XII)

$$R^3-COOR \qquad (XII)$$

in which $R^3$ has the abovementioned meaning and

R-represents hydrogen or a $C_1$-$C_6$-alkyl radical, are either directly reduced or compounds of the formula (XI) are first prepared by reduction and these are then oxidized.

The process according to the invention can be illustrated by way of example by the following equation:

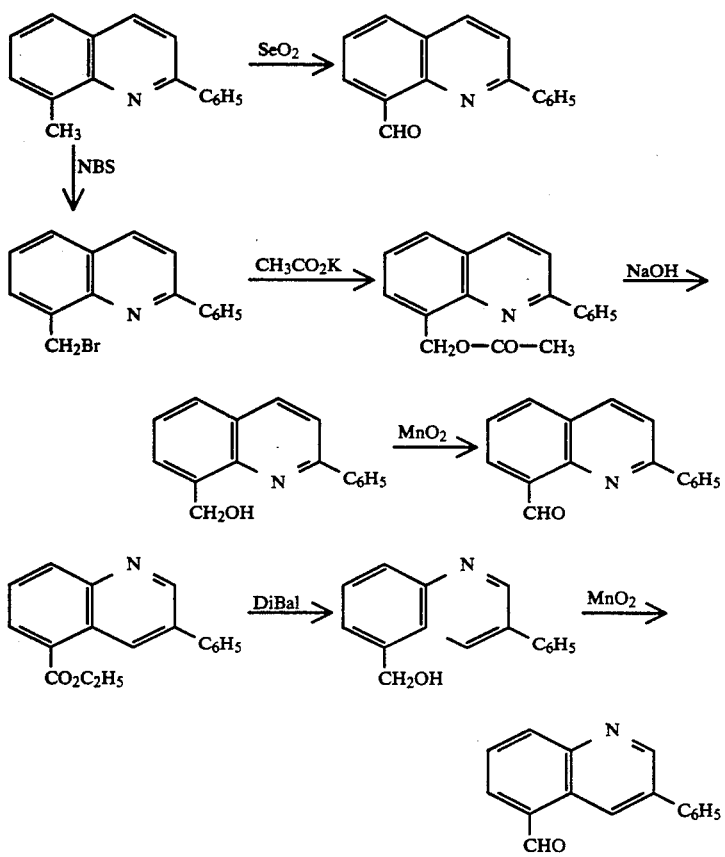

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoric triamide or dimethylformamide, or acetic acid and also methylene chloride, carbon tetrachloride or toluene. It is also possible to use mixtures of the solvents mentioned.

The compounds of the general formula (XII) are in general reduced using hydrides, preferably using sodium borohydride and diisobutylaluminum hydride in inert solvents such as ethers, hydrocarbons, halogenohydrocarbons or their mixtures, preferably in ethers such as, for example, diethyl ether, tetrahydrofuran or dioxane.

In the case of the compounds of the general formula (IX), suitable agents for the oxidation are, for example, chromyl chloride, ceric ammonium nitrate, silver(II) oxide, selenium dioxide or a chromium(VI) oxide in combination with acetic anhydride. Selenium dioxide is preferred.

Suitable oxidizing agents in the case of the hydroxymethyl compounds are, for example, manganese dioxide, dimethyl sulphoxide, ceric ammonium nitrate, dipyridine-chromium(VI) oxide, sodium dichromate, iodosobenzene, pyridine chlorochromate, silver carbonate on celite or Jones reagent.

The oxidations and reductions can be carried out at normal pressure or elevated or reduced pressure (for example from 0.5 to 50 bar), preferably at normal pressure.

The compounds of the general formula (IX) are known or can be prepared by conventional methods [compare J. Med. Chem. 32. 396–401 (1989)].

The compounds of the general formula (XII) are known in some cases (R≠H) [compare, however, J. Med. Chem. 16, 118–122 (1973), J. Med. Chem. 31, 1048–1052 (1988) and Monatssch. Chem., 114 (8–9), 1009–11], but can be prepared by known methods.

The compounds of the general formula (XII) are new in the case in which R represents hydrogen and $R^3$ denotes the radical of the formula

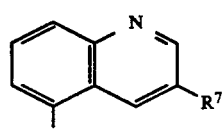

and can then be prepared via a new process by first reducing 4-nitro-3-hydroxyphthalide of the formula (XIII)

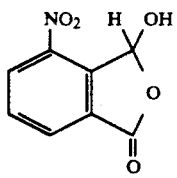

in inert solvents, preferably by hydrogenation in the presence of a catalyst, to give 4-amino-3-hydroxyphthalide of the formula (XIV)

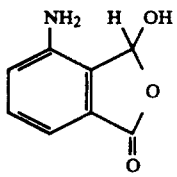

optionally isolating, or preferably reacting directly in solution with aldehydes of the general formula (XV)

$$R^7—CH_2—CHO \quad (XV)$$

in which $R^7$ has the abovementioned meaning, in inert solvents, if appropriate in the presence of a base.

Suitable solvents both for the hydrogenation and also for the further reaction are all organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoric triamide or dimethylformamide or acetic acid and also methylene chloride, carbon tetrachloride or toluene. It is also possible to use mixtures of the solvents mentioned. Methanol, ethanol, propanol or tetrahydrofuran are preferred.

The hydrogenation can be carried out at normal pressure or at elevated pressure, for example from 0.5 to 5 bar, preferably at atmospheric pressure.

The reduction is carried out in a temperature range from 0° C. to 80° C., preferably at room temperature.

Suitable catalysts are, in particular, palladium/barium sulphate. However, catalysts such as platinum, palladium, palladium on animal carbon or Raney nickel can also be employed.

The catalyst is employed in an amount of from 0.00001 to 1 mol, preferably from 0.0001 to 0.1 mol relative to 1 mol of the compound of the formula (XIII).

The compound of the formula (XIV) is new and can be prepared by the abovementioned method.

The compound of the formula (XIII) is known (compare T. Watanabe et al., Chem. Pharm. Bull., 20(10), 2123-2127 (1972)).

Suitable bases are, for example, triethylamine, 1,8-diazabicyclo[5.4.0]undec-7-ene, alkoxides such as sodium methoxide or carbonates such as sodium carbonate.

The base is employed in catalytic amounts, preferably using 0.001 mol to 0.1 mol relative to 1 mol of the compounds of the general formula (XV).

The aldehydes of the general formula (XV) are known or can be prepared by methods known from the literature (compare M. Elliott et al., Pestic. Sci. 18(4), 223-228 (1987)).

The acetoacetates of the formula (III) are known or can be prepared by customary methods [compare D. Borrmann, "Umsetzung von Diketonen mit Alkoholen, Phenolen und Mercaptanen" (Reaction of diketones with alcohols, phenols and mercaptans), in Houben-Weyl, Methoden der organischen Chemie (Methods of Organic Chemistry), Vol. VIII/4, 230 et seq. (1968)].

The ylidene compounds (IV) and (VII) are new, but can be prepared by customary methods [compare H. Dornow and W. Sassenberg, Liebigs Ann. Chem. 602, 14 (1957)].

The aminocrotonic acid derivatives of the formulae (VI) and (VIII) are known or can be prepared by known methods [S. A. Glickman, A. C. Cope, J. Am. Chem. Soc. 67, 1017 (1946)].

The compounds of the general formula (XI) are new and can be prepared by the abovementioned method.

The compounds of the general formula (V) are also known [compare N. Levy, C. W. Scaife, J. Chem. Soc. (London) 1946, 1100; C. D. Hurd, M. E. Nilson, J. Org. Chem. 20, 927 (1955)].

The existing preparation processes are only given for illustration. The preparation of the compounds of the formulae (I) and (II) are not restricted to these processes, but any modification of these processes can be used in the same manner for the preparation of the compounds according to the invention.

The compounds according to the invention exhibit an unforeseeable, useful pharmacological spectrum of action. They influence the contractility of the heart and the tone of the smooth musculature. They can therefore be employed in medicaments for influencing pathologically modified blood pressure, as coronary therapeutics and for the treatment of cardiac insufficiency. Moreover, they can be used for the treatment of cardiac arrhythmias, for the reduction of blood sugar, for the detumescence of mucosa and for influencing the salt and liquid balance.

The cardiac and vascular effects were found on isolated perfused guinea pig hearts.

To this end, the hearts of guinea pigs of 250 to 350 g weight are used. The animals are killed by a blow to the head, the thorax is opened, and a metal cannula is tied into the exposed aorta. The heart is separated out of the thorax with the lungs and connected to the perfusion apparatus via an aortic cannula with continuous perfusion. The lungs are separated at the roots of the lung. The perfusion medium used is a Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), the $CaCl_2$ content of which is 1.2 mmol/l. 10 mmol/l of glucose are added as an energy-producing substrate. The solution is filtered free from particles before perfusion. The solution is aerated with carbogen (95% $O_2$, 5% $CO_2$) to maintain the pH 7.4. The hearts are perfused with a constant flow (10 ml/min) at 32° C. by means of a peristaltic pump.

For the measurement of cardiac function, a liquid-filled latex balloon which is connected to a pressure transducer via a liquid column is inserted into the left ventricle through the left auricle, and the isovolumetric contractions are recorded on a rapid recorder (Opie, L., J. Physiol., 180 (1965), 529-541). The perfusion pressure is recorded by means of a pressure transducer which is connected to the perfusion system upstream of the heart. Under these conditions, a reduction in the perfusion pressure indicates a coronary dilation, and an increase or decrease in the left-ventricular contraction amplitude indicates a reduction or an increase in the heart contractility. The compounds according to the invention are perfused into the perfusion system in suitable dilutions just upstream of the isolated heart. Substance effects on the contraction amplitude of isolated guinea pig heart auricles at an active compound concentration of $10^{-4}$ g/l.

| Ex. No. | % change in the ventricular pressure amplitude |
|---|---|
| 3 | +129 |
| 8 | +129 |
| 29 | +170 |
| 30 | +79 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to attain the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intraveneously.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may sometimes be necessary to deviate from the amounts mentioned, in particular depending on the body weight and on the type of administration routes, on individual behavior towards the medicament, the nature of its formulation and the time or interval at which administration takes place. Thus, in some cases it may be sufficient to manage with less than the minimum amount previously mentioned, while in other cases the upper limit mentioned must be exceeded. In the case of the administration of larger amounts, it may be necessary to divide these into several individual doses over the course of the day.

EXAMPLE I

4-Amino-3-hydroxyphthalide

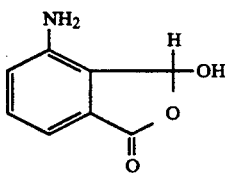

10 g of 3-hydroxy-4-nitro-phthalide are dissolved in 100 ml of tetrahydrofuran and hydrogenated at atmospheric pressure and at 20-35° C. after adding 1 g of palladium on barium sulphate (5%). The catalyst is filtered off and the filtrate is concentrated. The evaporation residue is stirred with ether and filtered with suction. 5.8 g (68.5% of theory) of a colorless substance of melting point 280–285° C. (dec.) are obtained.

EXAMPLE II

3-Phenyl-quinoline-5-carboxylic acid

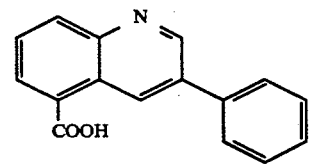

50 g (0.256 mol) of 3-hydroxy-4-nitro-phthalide are hydrogenated at 20° C. and at 3 bar using 5 g of Pd/barium sulphate (5%) in 380 ml of ethanol. The mixture is filtered with suction, and 0.308 mol=38.7 ml of phenylacetaldehyde solution are added to the filtrate. The mixture is boiled for 4 hours, the quinolinecarboxylic acid precipitating. It is cooled, filtered with suction and washed with ethanol. 28.3 g (44.3% of theory) of a colorless compound of melting point>290° C. are obtained.

EXAMPLE III

5-Hydroxymethyl-3-phenyl-quinoline

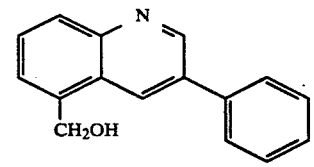

80 g (0.32 mol) of 3-phenyl-quinoline-5-carboxylic acid are suspended in 1.6 l of abs. tetrahydrofuran under argon and 400 ml of 1 molar lithium aluminum hydride solution in tetrahydrofuran are added dropwise. In this process, the temperature may rise to 35° C. The mixture is subsequently stirred for 90 minutes and 16 ml of water and then 48 ml of saturated ammonium chloride solution are added dropwise with cooling, the mixture is subsequently stirred for 30 minutes and filtered with suction, the solid is washed with tetrahydrofuran and the filtrate is concentrated. About 80 g of crude product are obtained. The melting point of the purified compound is 110–112° C.

EXAMPLE IV

2-Phenyl-quinoline-8-aldehyde

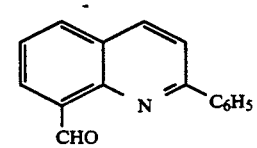

8.46 g of 8-methyl-2-phenylquinoline [compare Atwell, G. J. et al., J. Med. Chem. 32, 396–401 (1989)] are mixed with 8.9 g (80 mmol) of selenium dioxide and heated first to 140° C. with stirring, then to 160° C. for 5 hours. The mixture is cooled, a further 2.5 g of selenium dioxide are added and the mixture is stirred at 160° C. for 2.5 hours. It is cooled, stirred with methylene chloride, the solid is filtered off and the filtrate is concentrated. The mixture obtained is purified by flash chromatography on silica gel using toluene/hexane 1:1 and toluene. 3.9 g of beige-colored crystals of melting point 100–102° C. are obtained.

EXAMPLE V

3-Phenyl-quinoline-5-aldehyde

34.5 g (124.5 mmol) of ethyl 3-phenyl-quinoline-5-carboxylate [compare Makriyanmis, A. et. al., J. Med. Chem. 16, 118–122 (1973)] are dissolved in 800 ml of dry methylene chloride and cooled to about −70° C. 406 ml of 1 molar DIBAL solution are added dropwise under argon in toluene at this temperature. The mixture is subsequently stirred at −70° C. for 2.5 hours and 40 ml of water is then cautiously added dropwise. 200 ml of saturated sodium chloride solution are added dropwise. The mixture is allowed to come to room temperature slowly and is stirred overnight. The salt formed is filtered off with suction and washed with methylene chloride. The filtrate is shaken once with water, dried and concentrated. 33 g of an oil are obtained which is dissolved in 600 ml of methylene chloride and, after adding 150 g of manganese dioxide, the solution is boiled for 3 hours. It is cooled and filtered with suction. Tonsil is added to the filtrate, and the mixture is filtered and concentrated again. 28.2 g of beige-colored product of melting point 122–124° C. are obtained.

PREPARATION EXAMPLES

Example 1

Preparation method B

Methyl 1,4-dihydro-2,6-dimethyl-3-nitro-4-(3-phenyl-quinolin-5-yl)-pyridine-5-carboxylate

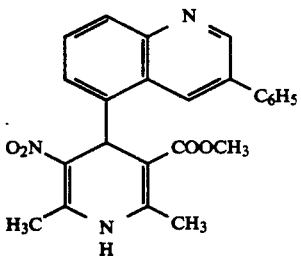

0.9 g (8.75 mmol) of nitroacetone, 0.58 g (5 mmol) of methyl 3-aminocrotonate and 0.3 ml (5 mmol) of acetic acid are added to 1.17 g (5 mmol) of 3-phenylquinoline-5-aldehyde in 10 ml of ethanol and the mixture is boiled for 1 hour. It is cooled and concentrated. The evaporation residue is purified by means of a silica gel column using chloroform/methanol mixtures. The clean fractions are concentrated, and the evaporation residue is recrystallized from ethyl acetate. 0.6 g of orange-colored crystals of melting point 262° C. are obtained.

Example 2

Preparation method A 1,4-Dihydro-2,6-dimethyl-3-methoxycarbonyl-4-(3-phenylquinolin-5-yl)-pyridine-5-carbonitrile

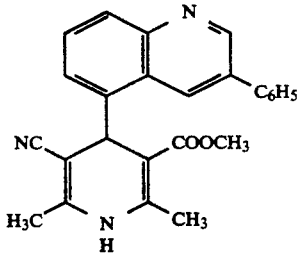

0.7 g (3 mmol) of 3-phenylquinoline-5-aldehyde in 6 ml of ethanol are boiled with 0.35 g (3 mmol) of methyl acetoacetate and 0.25 g (3 mmol) of 3-aminocrotononitrile for 24 hours. The mixture is cooled and concentrated. The evaporation residue is purified by means of a silica gel column using toluene/ethyl acetate mixtures. The clean fractions are combined and concentrated. 0.5 g of colorless substance of melting point 242° C. are obtained by crystallization from isopropanol.

EXAMPLE 3

Ethyl 2-methyl-4-(3-phenyl-quinolin-5-yl)-5-oxo-1,4,5,7-tetrahydrofuro[3,4-b]-pyridine-3-carboxylate

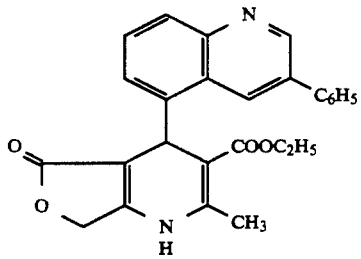

1.4 g (6.0 mmol) of 3-phenylquinoline-5-aldehyde in 20 ml of ethanol are boiled with 0.79 ml (6.2 mmol) of ethyl acetate and 1.16 g (6.2 mmol) of ethyl 3-amino-4-acetoxycrotonate for 2 days. The mixture is cooled and concentrated. The residue is coarsely purified by flash chromatography. The intermediate obtained is boiled in a solution of 970 mg of potassium hydroxide in 50 ml of methanol for 40 minutes. The mixture is cooled, adjusted to pH 5 with 10% strength hydrochloric acid and concentrated, the residue is taken up in ethyl acetate and the solution is washed with water. The organic phase is dried and concentrated. The residue is freed from by-products by column chromatography, and the fractions are concentrated and crystallized from acetonitrile. 460 mg of colorless crystals of melting point 257–260° C. are obtained.

The compounds shown in Table 1 were prepared in analogy to the procedure of Examples 1, 2 and 3:

TABLE 1

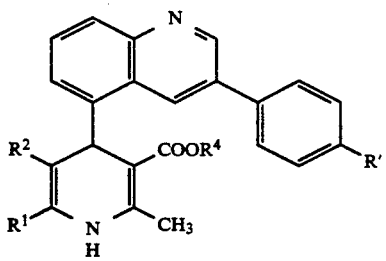

| Ex. No. | R¹ | R² | R⁴ | R' | m.p. (°C.) |
|---|---|---|---|---|---|
| 4 | CH₃ | NO₂ | —CH(CH₃)₂ | H | 252 |
| 5 | CH₃ | CN | —C₂H₅ | H | 218 |
| 6 | CH₃ | CN | —CH(CH₃)₂ | H | 239 |
| 7 | CH₃ | NO₂ | —C₂H₅ | H | 263 |
| 8 | O=C-O-CH₂CH₃ | | —CH₃ | H | 260 |
| 9 | O=C-O-CH₂CH₃ | | —CH(CH₃)₂ | H | 248 |
| 10 | CH₃ | CN | —CH(CH₃)₂ | H | (−)-enant. 178° C. |
| 11 | CH₃ | CN | —CH(CH₃)₂ | H | (+)-enant. 178° C. |
| 12 | CH₃ | CN | —CH₂CH(CH₃)₂ | H | 257–259 |
| 13 | CH₃ | CN | —CH(CH₃)₂ | F | (−)-enant. 209° C. |
| 14 | CH₃ | CN | —CH(CH₃)₂ | F | 213 |
| 15 | CH₃ | CN | —CH(CH₃)—COOC₂H₅ | H | 205–211 |
| 16 | CH₃ | CN | —CH(CH₃)—CO₂—CH₂—CH(CH₃)₂ | H | 157–158 |
| 17 | CH₃ | CN | —(CH₂)₂—CH₃ | H | 237 |
| 18 | CH₃ | CN | —(CH₂)₂—O—CO—CH₃ | H | 201–203 |
| 19 | CH₃ | CN | —(CH₂)₂—OCH₃ | H | 222 |
| 20 | CH₃ | CN | —(CH₂)₂—CN | H | dec. 193 |
| 21 | CH₃ | CN | —(CH₂)₂—O—C₂H₅ | F | 216–218 |
| 22 | CH₃ | CN | —CH₃ | H | (−)-enant. 264° C. |
| 23 | CH₃ | CN | —C₂H₅ | H | (−)-enant. 213° C. |
| 24 | CH₃ | CN | H | H | 244–246 |
| 25 | CH₃ | CN | —(CH₂)₂—OH | H | 225–226 |

EXAMPLE 26

Isopropyl 1,4-dihydro-2,6-dimethyl-3-nitro-4-(2-phenylquinolin-8-yl)-pyridine-5-carboxylate

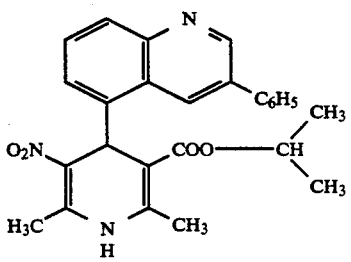

1.17 g (5 mmol) of 2-phenyl-quinoline-8-aldehyde are boiled in 10 ml of ethanol with 0.9 g (8.75 mmol) of nitroacetone, 0.72 g (5 mmol) of ispropyl 3-aminocrotonate and 0.3 ml (5 mmol) of acetic acid for 1 hour. The precipitated crystals are filtered with suction after cooling and washed with ethanol. 1.1 g of orange-colored crystals of melting point 205° C. are obtained.

The compounds shown in Table 2 were prepared in analogy to the procedure of Example 26:

TABLE 2

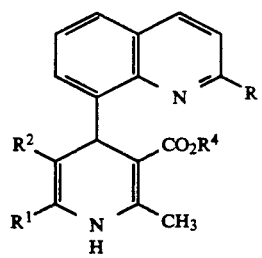

| Ex. No. | $R^1$ | $R^2$ | $R^4$ | R | m.p. °C.) |
|---|---|---|---|---|---|
| 27 | ethoxycarbonyl (O=C-O-Et) | | —$C_2H_5$ | 4-F-phenyl | 275–276 |
| 28 | $CH_3$ | $NO_2$ | —$C_2H_5$ | 4-F-phenyl | 275–277 |

TABLE 2-continued

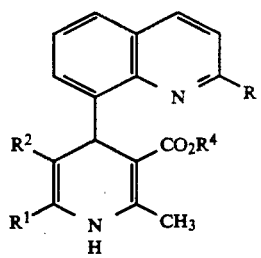

| Ex. No. | $R^1$ | $R^2$ | $R^4$ | R | m.p. °C.) |
|---|---|---|---|---|---|
| 29 | $CH_3$ | $NO_2$ | —$CH_3$ | 4-F-phenyl | 237 |
| 30 | ethoxycarbonyl (O=C-O-Et) | | —$C_2H_5$ | 2-pyridyl | 281 |

The compounds shown in the Tables 3, 4 and 5 were prepared analogy to the procedure of Example 2.

TABLE 3

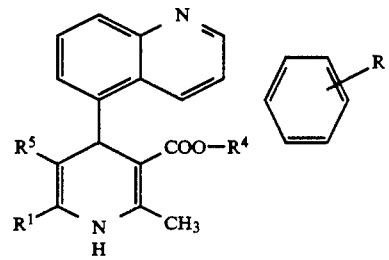

| Ex. No. | $R^1$ | $R^2$ | $R^4$ | R | m.p. (°C.) | $R_f$ (toluene-ethyl acetate 1:1) |
|---|---|---|---|---|---|---|
| 31 | $CH_3$ | CN | $-CH(CH_3)COOCH_3$ | H | — | 0.22/0.29 |
| 32 | $CH_3$ | CN | $-CH(CH_3)COO-CH(CH_3)_2$ | H | 237–40 (+)-enant. | 0.31 |
| 33 | $CH_3$ | CN | —$(CH_2)_2$—O—$C_2H_5$ | H | 232 | |
| 34 | $CH_3$ | CN | —$(CH_2)_2$—O—$CH(CH_3)_2$ | H | 236 | |
| 35 | $CH_3$ | CN | $-CH(CH_3)COOH$ | H | 186–88 (−)-enant. | |
| 36 | $CH_3$ | CN | $-CH(CH_3)COOH$ | H | 180 dec. (+)-enant. | |
| 37 | $CH_3$ | CN | $-CH(CH_3)COOCH_3$ | H | 162 (−)-enant. | 0.29 |

TABLE 3-continued

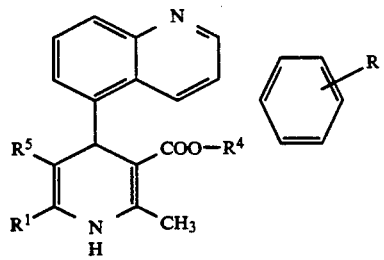

| Ex. No. | R¹ | R² | R⁴ | R | m.p. (°C.) | $R_f$(toluene-ethyl acetate 1:1) |
|---|---|---|---|---|---|---|
| 38 | CH₃ | CN | —CH(CH₃)—COOCH₃ | H | (+)-enant. | 0.22 |
| 39 | CH₃ | CN | —CH(CH₃)—COO—CH₂—CH(CH₃)₂ | H | — | 0.31 |
| 40 | CH₃ | CN | —CH₂—CH₂—CH₃ | H | 121 (−)-enant. | |
| 41 | CH₃ | CN | —CH₂—CH₂—CH₂—CH₃ | H | 225 (−)-enant. | |
| 42 | CH₃ | CN | —CH(CH₃)—COOH | 4-F | 182 (−)-enant. | |
| 43 | CH₃ | CN | —CH₂—CH₂—CH₃ | 4-F | 115 (−)-enant. | |
| 44 | CH₃ | CN | —CH₃ | 4-F | 245 (−)-enant. | |
| 45 | CH₃ | CN | —CH₂—CH₃ | 4-F | 143 (−)-enant. | |
| 46 | CH₃ | CN | —CH₂—CH₂—CH₂—CH₃ | 4-F | 204(−)-enant. | |
| 47 | CH₃ | CN | —CH₂—CH₃ | 4-CH₃ | 235 | |
| 48 | CH₃ | CN | —CH(CH₃)₂ | 4-CH₃ | 242 | |
| 49 | CH₃ | CN | —CH₂—CH₂—CH₃ | 4—CH₃ | 236 | |
| 50 | CH₃ | CN | —CH₃ | 2-Cl | 249 | |
| 51 | CH₃ | CN | —CH(CH₃)₂ | 2-Cl | 179–81 | |
| 52 | CH₃ | CN | —CH₂—CH₃ | 2-Cl | 213 | |
| 53 | CH₃ | CN | —CH₂—CH₂—CH₃ | 2-Cl | 139 | |
| 54 | CH₃ | CN | —CH₃ | 2-F | 144–146 | |
| 55 | CH₃ | CN | —CH₂—CH₃ | 2-F | 181–83 | |
| 56 | CH₃ | CN | —CH(CH₃)₂ | 2-F | 192–94 | |
| 57 | CH₃ | CN | —(CH₂)₂OCH₃ | H | 173 (−)-enant. | |
| 58 | CH₃ | CN | —CH(CH₃)₂ | m-F | 249 | |
| 59 | CH₃ | CN | —CH₂—CH(CH₃)₂ | H | 248 (−)-enant. | |
| 60 | CH₃ | CN | —C₂H₅ | m-F | 210–212 | |
| 61 | CH₃ | CN | —(CH₂)₂—CH₃ | m-Cl | 214 | |
| 62 | CH₃ | CN | —(CH₂)₂—OC₂H₅ | H | 168 (−)-enant. | |
| 63 | CH₃ | CN | —CH(CH₃)₂ | m-Cl | 270 | |
| 64 | CH₃ | CN | —CH₃ | m-Cl | >128 (decomp.) | |
| 65 | CH₃ | CN | —C₂H₅ | m-Cl | 245 | |

TABLE 4

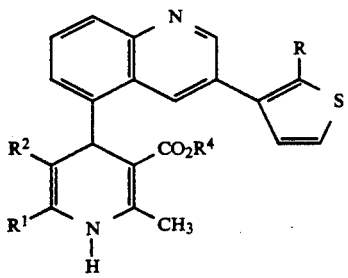

| Ex. No. | R¹ | R² | R⁴ | R | m.p. (°C.) |
|---|---|---|---|---|---|
| 66 | CH₃ | NO₂ | —C₂H₅ | H | 246 (decomp.) |
| 67 | CH₃ | NO₂ | —CH(CH₃)₂ | Cl | 239 |

TABLE 5

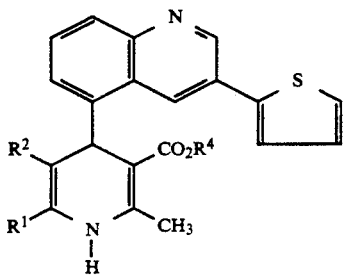

| Ex. No. | R¹ | R² | R⁴ | m.p. (°C.) |
|---|---|---|---|---|
| 68 | CH₃ | NO₂ | —CH(CH₃)₂ | 265 (decomp.) |

It will be appreciated that the instant specification is set forth by way of illustration and not limitation, and that varous modifications and changes may be made without departing from the spirit and scope of the present invention.

What is claimed is:

1. An aldehyde of the formula $$R^3-CHO \quad (II)$$

in which
R³ represents a radical of the formula

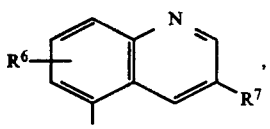

-continued

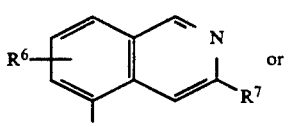 or

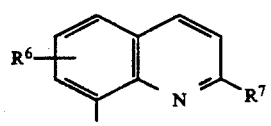

in which
R⁶-denotes hydrogen, halogen or straight-chain or branched alkyl or alkoxy in each case having up to 8 carbon atoms,
R⁷-denotes aryl having 6 to 10 carbon atoms, which is optionally monosubstituted or disubstituted by identical or different substituents from the group consisting of halogen, nitro, cyano, trifluoromethyl, trifluoromethoxy, trifluoromethylthio, straight-chain or branched alkyl, alkoxy or alkoxycarbonyl in each case having up to 8 carbon atoms and carboxyl, or denotes thienyl or pyridyl, which are optionally monosubstituted by halogen.

2. A compound according to claim 1, in which
R⁶ denotes hydrogen, chlorine or methyl, and
R⁷ denotes phenyl which is optionally substituted by fluorine, chlorine, nitro, trifluoromethyl or by straight-chain or branched alkyl or alkoxy in each case having up to 4 carbon atoms, or denotes thienyl or pyridyl, which are optionally monosubstituted by fluorine or chlorine.

3. A compound according to claim 1, wherein such compound is 3-phenyl-5-formyl-quinolone of the formula

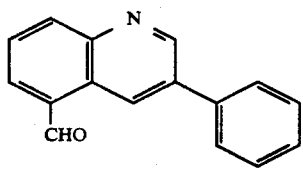

4. A compound according to claim 1, wherein such compound is 3-(4-fluorophenyl)-5-formyl-quinoline of the formula

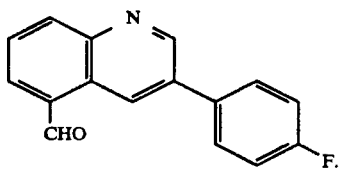

* * * * *